United States Patent [19]
Morrison et al.

[11] Patent Number: 5,211,887
[45] Date of Patent: May 18, 1993

[54] HIGH PURITY ALKYLLITHIUM COMPOUNDS AND PROCESS OF PREPARATION

[75] Inventors: Robert C. Morrison, Gastonia; B. Troy Dover, Kings Mountain; Conrad W. Kamienski, Gastonia, all of N.C.

[73] Assignee: FMC Corporation, Philadelphia, Pa.

[21] Appl. No.: 749,245

[22] Filed: Aug. 22, 1991

Related U.S. Application Data

[63] Continuation-in-part of Ser. No. 621,147, Nov. 29, 1990, abandoned.

[51] Int. Cl.$^5$ .................................................. C07F 1/02
[52] U.S. Cl. .................................................. 260/665 R
[58] Field of Search ..................................... 260/665 R

[56] References Cited

U.S. PATENT DOCUMENTS 3,122,592  2/1964  Eberly ................................. 260/665
3,293,313  12/1966  Borkowski ........................... 260/665

OTHER PUBLICATIONS

Stiles et al., Journal of American Chemical Society, vol. 81, pp. 1497–1503 (1959).
Lochmann et al., Journal of Organometallic Chemistry, vol. 326, pp. 1–7 (1987).
Bell et al., Journal of Organic Chemistry, vol. 24, pp. 2036–2037 (1959).
Smith, Journal of Organometallic Chemistry, vol. 82, pp. 1–6 (1974).
Kamienski et al., Journal of Organic Chemistry, vol. 25, pp. 1807–1808 (1960).

*Primary Examiner*—José G. Dees
*Assistant Examiner*—Porfirio Nazario
*Attorney, Agent, or Firm*—Charles C. Fellows; Robert L. Andersen; Robert C. Morrison

[57] ABSTRACT

A process for the preparation of alkyllithium compounds including 2-alkyl-substituted alkyllithium compounds by reacting in a liquid organic solvent, in an inert atmosphere a $C_2$ to $C_{18}$ saturated, acyclic, primary alkyl halide including 2-alkyl-substituted alkyl halides with a dispersion of particulate lithium and sodium metals in which there is 5 to 50 mole percent sodium based on the lithium content at a temperature of 0° to a temperature up to but not exceeding the decomposition temperature of the product.

8 Claims, No Drawings

HIGH PURITY ALKYLLITHIUM COMPOUNDS AND PROCESS OF PREPARATION

This invention is a continuation-in-part of application Ser. No. 621,147, filed Nov. 29, 1990, (now abandoned), and is concerned with high purity alkyllithiums particularly 2-alkyl-substituted alkyllithiums, and a process for their preparation via reaction of the appropriate alkyl halide with a dispersion of a mixture of sodium and lithium metals.

Branched and 2-alkyl-substituted alkyllithiums such as isopropyl, isobutyl, or 2-ethylhexyllithium and the like are difficult or impossible to synthesize via conventional lithium metal-alkyl halide methods due to the slow reaction rate or non-reactivity of the reagents. Repeated attempts to synthesize 2-ethylhexyllithium (EHL) with or without catalysts, in refluxing pentane which is known to be beneficial in the preparation of alkyllithiums such as t-butyllithium, activation of the lithium with alkyllithium and pre-initiation with n-butyl chloride, etc., have resulted in little or no reaction (see W. N. Smith, Jr., *J. Organometallic Chem.* 82 (1974) 1–6). See also L. Lochmann et al., *J. Organometallic Chem.* 326 (1987) 1–7 who reported low yields, product containing unreacted 2-ethylhexyl chloride and long induction periods (as much as ten hours) prior to initiation when treating 2-ethylhexyl chloride (EHC) with lithium metal powder in hexane. These compositions are very difficult to purify by standard methods due to the high boiling point of 2-ethylhexyl chloride (170° C.) and the low decomposition temperatures of alkyllithium causing them to decompose during purification.

The use of mixtures of sodium and lithium metals in preparing organometallic compounds is not new.

W. L. Borkowski, in U.S. Pat. No. 3,293,313, issued Dec. 20, 1966, teaches the use of equimolar quantities of sodium and lithium with a minimum of ⅓ mole of sodium per mole of lithium (Li/Na=67:33) in preparing organo-lithium compounds such as n-butyllithium.

K. C. Eberly, in U.S. Pat. No. 3,122,592 patented Feb. 25, 1964, disclosed the use of 0.3 to 1 percent by weight of sodium alloyed with the lithium accelerates the reaction with the alkyl chloride.

The beneficial effect of adding small amounts of sodium metal to lithium metal in the preparation of n-butyllithium from n-butyl bromide in diethyl ether is described by J. A. Beel, et al. in J. Org. Chem 24, 2036 (1959). Similarly, C. W. Kamienski and D. L. Esmay, J. Org. Chem, 25, 1807 (1960) describe the beneficial effect of added sodium (0.02%) in preparing p-dimethylaminophenyllithium; and, M. Stiles and R. P. Mayer, J. Am. Chem. Soc., 81, 1497 (1959) describe the beneficial effect of added sodium in the range of 1–2% in the preparation of t-butyllithium.

Borkowski in U.S. Pat. No. 3,293,313 shows no advantage other than a cost advantage in using sodium in a molar percentage range, based on lithium, of 33 to 50% or more in preparing n-butyllithium.

The present invention provides a process for preparing alkyllithiums including 2-alkyl substituted alkyllithium compounds in high yields and high purity, with good reaction rates, comprising reacting, in a liquid organic solvent, a $C_2$ to $C_{12}$ linear or to $C_{18}$ 2-alkyl-substituted, saturated, acyclic, primary alkyl halides with a dispersion of both lithium and sodium metals, which dispersion contains a significant amount of sodium metal, at temperatures between 0° C. and about 70° C.; higher temperatures, but below the decomposition temperature of the product, can be employed but are not necessary. Sodium is present in the dispersions in amounts of 5 to about 33 mole percent and lithium in amounts of 95 to 67 mole percent. The reaction is conducted in an inert atmosphere. Surprisingly, the product and by-product alkalimetal chlorides are easily separated by filtration.

While temperatures up to just below the decomposition temperatures of the products can be employed lower temperatures between 20° C. and 70° C. are preferred and temperatures between 30° C. and 40° C. are most preferred. It is well known in organolithium processing that these exothermic reactions can be at least partially controlled by operating at the reflux temperature of the reaction medium. This removes heat as it is produced and so helps prevent Wurtz coupling which reduces yields. Thus, refluxing pentane is a preferred solvent. Other solvents are useful even though they are not refluxed; for example cyclohexane (in this context termed a "non-refluxing solvent") is a useful solvent even though its boiling point is too high to be used at the reflux temperature in view of the decomposition temperature of a product such as 2-ethylhexyllithium.

The lithium and sodium metals are introduced to the reaction dispersed in a solvent, preferably the solvent in which the reaction will be conducted. The metals are preferably in particulate form; powder (about 90 μm to about 850 μm), sand (about 850 μm to about 2 mm), or shot (about 2 mm to about 6.7 mm). While coarser granular forms of the metals may be employed, the coarser materials generally result in longer reaction times. The dispersed metals are preferably conditioned or activated by treating them with alkyllithium and agitation in a solvent, preferably a suitable reaction solvent for 1–2 hours before use. The metal dispersions may be prepared individually and then mixed or may be prepared simultaneously in the same dispersion apparatus.

A dispersion of lithium and sodium metals containing a significant amount of sodium reacts sufficiently with a 2-alkyl-substituted alkyl halide to produce the corresponding 2-alkyl substituted alkyllithium and by-product lithium and sodium halides. For example, 2-ethylhexyl chloride (EHC) in a hydrocarbon solvent with a dispersion of a mixture of lithium and sodium metals reacts to produce 2-ethylhexyllithium (EHL) in good yield. The following chemical equation represents the reaction:

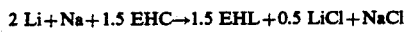

$$2\ Li + Na + 1.5\ EHC \rightarrow 1.5\ EHL + 0.5\ LiCl + NaCl$$

As the following Examples A and B and Table I show, 2-ethylhexyllithium can be prepared in good yield and quality and is essentially free of alkylsodium. The reaction proceeds to completion in a refluxing solvent (pentane) as well as in a "non-refluxing solvent" (cyclohexane) (see Table I). The reaction does not proceed in the absence of sodium (see Example B). The sodium can be varied from about 5 mole % to about 40 mole % (based on lithium) with optimum yields being achieved at about 17 mole % sodium. (See Table I, Experiments Example No. 6708 and Example No. 361-29.) Filtrations of all final products were rapid.

Utility for these 2-alkyl-substituted alkyllithium compounds is to generate hydrocarbon soluble dialkylmagnesium and lithium trialkylmagnesiate compounds. As the following equation shows, another utility of 2-ethylhexyllithium would be as the source of the super base, 2-ethylhexylpotassium which is soluble in hexane:

$$R^1Li + R^2OK \rightarrow R^1K + R^2OLi$$

For example, employing 2-EHL and potassium t-pentyloxide results in a homogenous system in hexane thus, permitting easy isolation of the product by metallation of a third component. 2-Ethylhexyllithium employed in metallation reactions (metal-hydrogen exchange) would produce non-volatile 2-ethylhexane (boiling point equals 119° C.) versus volatile butane (boiling point equals −0.5° C.) when n-butyllithium is used. 2-Ethylhexyllithium at 95 weight percent is a liquid whereas n-octyllithium is a solid. Surprisingly, 2-ethylhexyllithium in all concentrations is not pyrophoric whereas as little as 8 weight percent of n-butyllithium in a liquid hydrocarbon solvent is pyrophoric. Thus, a commercially pure 2-ethylhexyllithium product could be sold to and dissolved by a customer in the solvent of his choice. The 2-ethylhexyl chloride is relatively inexpensive, so 2-ethylhexyllithium could be used as a substitute for n-butyllithium which is sold in substantial amounts by the alkyllithium industry as a pyrophoric 15 weight percent solution in various liquid hydrocarbon solvents.

The alkyl halides useful in practicing this invention include but are not limited to $C_4$ to $C_{18}$ 2-alkyl-substituted, saturated acyclic, primary alkyl halides, preferably chlorides, iodides and bromides, and for reasons of cost, most preferably chlorides such as 1- bromo-2-methylpentane, 1-chloro-2-methylpentane, 1- chloro-2-ethylhexane, 1-bromo-2-ethylhexane, 1-chloro-2,2-dimethylpropane, 1-bromo-2,2-dimethylpropane and the like. Preferred alkyl halides contain 5 to 10 carbon atoms. Other alkyl halides are $C_2$ to $C_{12}$ linear primary alkyl halides such as chloroethane, 1-chlorobutane, 1-chlorohexane, and 1-chlorooctane.

The liquid hydrocarbon solvents useful in practicing this invention include, but are not limited to, aliphatic hydrocarbons containing 5 to 10 carbon atoms, alicyclic hydrocarbons containing 5 to 10 carbon atoms and aromatic hydrocarbons containing 6 to 10 carbon atoms. Examples of these liquid hydrocarbon solvents are pentane, n-hexane, n-heptane, mixed paraffinic hydrocarbons having boiling points below 130° C., cyclohexane, methylcyclohexane, benzene, toluene, ethylbenzene, xylene, cumene, mixtures thereof and so forth.

Those skilled in the art will appreciate that advantages of the present invention include:

1. Preparation of alkyllithiums which were previously impossible to prepare in good yield, high purity, and low organic and inorganic halide content.
2. Use of inexpensive sodium in place of part of the lithium.
3. Direct one-step, one-reactor synthesis.
4. Easy separation of product from by-product by filtration.

The conventional method for preparing alkyllithium compounds which involves the use of lithium containing small amounts of sodium (<1 mole %) has failed to generate 2-ethylhexyllithium in good yield and high purity. The new method described herein also applies to the preparation of other organolithium compounds which are also difficult or impossible to synthesize by the conventional method.

There are several advantages in the use of admixed sodium metal when preparing alkyllithium compounds from lithium metal dispersions and alkyl chlorides.

Among these are, as has already been shown, an increased yield of product or an enhanced ability to prepare the product where it could not previously be made (2-ethylhexyllithium). Thus, e.g., a 70% yield of n-octyllithium was prepared in hexane without any sodium present. On addition of at least 10 mole percent of sodium, the yield rises to 88%. (See Table V.) The use of aliphatic solvents in these cases causes precipitation of the intermediate n-octylsodium, but use of toluene circumvents this difficulty since the n-octylsodium in soluble toluene, thus allowing the metal-metal exchange reaction to proceed to completion.

Aside from the greater ease of initiating reactions between lithium metal and alkyl chlorides, the presence of added sodium promotes the reaction and provides a more complete reaction, resulting in the presence of significantly less unreacted halide in the product solution and, therefore, a decreased tendency to post-react with the product alkyllithium to give a precipitate of LiCl (see n-octyl runs in Table V; see also 2-ethylhexyl runs in Table I).

The added sodium also provides for a much decreased content of dissolved lithium chloride in the product alkyllithium solutions, obtained from reaction of lithium metal with alkyl chlorides in hydrocarbon solvents. Tables IV and V show this effect for various alkyllithiums. Coupled with the presence of little or no unreacted alkyl chloride, the alkyllithium solutions show little tendency to precipitate lithium chloride, and thus, maintain their clarity relative to those solutions not generated by the use of added sodium.

The post-reactive coupling of alkyl chlorides mentioned above can raise the soluble LiCl level to an extent which causes super saturation of the solution and a greater tendency to form LiCl precipitates on cooling and especially on concentration of these solutions. This precipitation of LiCl causes a haziness to appear in solution. The use admixed sodium prevents this condition from occurring and maintains solution clarity. Also, precipitates of LiCl cause plugging of discharge lines and valves.

The presence of dissolved LiCl can also cause unknown deleterious effects when these alkyllithium solutions are utilized, e.g., in polymerization initiation and stereochemical syntheses.

Thus, these alkyllithium solutions produced via admixture of sodium are purer, and are of higher quality.

This invention concerns a novel method of preparation for 2-ethylhexyllithium which previously has been difficult or impossible to prepare in good yield in hydrocarbon solvent employing alkyl halides and lithium. This is achieved by incorporating a significant amount of sodium dispersion of 5 up to about 33 mole %, preferably 10 to 30 mole % and most preferably 15 to 20 mole % with a corresponding amount of lithium dispersion to provide 100 mole mole percent total; thereafter the reaction between 2-ethylhexyl chloride and the metals proceeds efficiently to produce hydrocarbon soluble 2-ethylhexyllithium. Sodium is converted to insoluble sodium chloride via metal/metal exchange reactions and is removed along with lithium chloride and residual metals by filtration. Under optimum conditions employing an 83/17 molar ratio of lithium and sodium, EHL solutions are obtained which contain low levels of soluble inorganic compounds (See Table I—Examples 6708 and 361-29). The lithium and sodium dispersions can be prepared separately and then mixed prior to reaction or can be dispersed together in the same pot. Also, the reaction can be carried out efficiently in refluxing or so called "non-refluxing solvents" with optimum yields being 90 to 95% when employing lithium/sodium dispersion (83/17 mole %) and with little or no residual alkyl halide remaining in solution. Thermal stability testing indicates 2-ethylhexyllithium to be comparable to n-butyllithium in stability.

The following Examples further illustrate the invention. All the reactions are conducted in, and the metals and products stored in, an inert atmosphere, generally argon. All reaction equipment used in the Examples was baked at 150° C. overnight, assembled hot, and then purged with argon until cool.

EXAMPLES

Synthesis of 2-Ethylhexyllithium (EHL) via the Alkyl Chloride and a Mixture of Sodium and Lithium Dispersion 2-Ethylhexyllithium (EHL) is synthesized via the following metal/alkyl chloride exchange reaction(s):

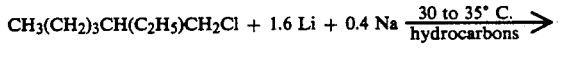

$$CH_3(CH_2)_3CH(C_2H_5)CH_2Li + 0.6 \, LiCl + 0.4 \, NaCl$$

This particular alkyl halide will not readily react with lithium dispersion alone; however, with sodium dispersion present, the reaction proceeds to completion. The halide is added dropwise over a period of two to three hours. This reaction is exothermic and requires cooling in order to maintain the reaction temperature between 30° to 35° C. Several hours of post reaction time, with stirring, are required to deplete any residual alkyl chloride which may be present.

Filtration yields a colorless to light yellow solution of EHL in hydrocarbon solvent. The EHL content is determined by Total Alkalinity Titration and Active Carbon-Lithium Titration (W. E. Titration). Analysis for sodium and inorganic chloride content are done by Atomic Adsorption Spectroscopy and Mohr Titration, respectively. The lithium and sodium dispersion can be prepared jointly in the same reaction vessel or can be prepared separately and then mixed.

A. Synthesis of 2-Ethylhexyllithium (EHL) (exemplary Run 361-29

Preparation of Sodium Metal Dispersion

Sodium metal (0.24 moles) was charged to a 500 ml, flask along with n-heptane (100 ml) and 25 ml of Unocal 66/3 solvent (by volume %: 25.9 n-paraffins, 22.5% isoparaffins, 10.7% cyclopentanes, 38.8% cyclohexanes, 2.0% cycloparaffins and 0.1% aromatics). The mixture was heated with the heating mantle to 105° C. and then stirred vigorously for four minutes. Stirring was stopped, and the sodium dispersion was cooled quickly to ambient by means of a Dry Ice/hexane cooling bath. The resultant sodium dispersion was washed by decantation with two 75 ml aliquots of pentane and then transferred to the EHL reaction vessel along with 100 ml of pentane.

Preparation of 2-Ethylhexyllithium (EHL)

Previously prepared lithium dispersion (1.17 moles) was washed with two 100 ml aliquots of pentane in a glass filter funnel and then transferred along with 225 ml of pentane and 10 ml of EHL in pentane to the reaction vessel containing the sodium dispersion prepared above. The resultant slurry was stirred for one hour in order to condition (activate) the metals. The reaction mass was heated to reflux (38.1° C.) and then initiated by the addition of 2 grams of 2-ethylhexyl chloride. The remaining halide (72.3 g) was then added at a constant rate sufficient enough to keep the reaction medium at reflux. The total halide addition time was 77 minutes. After halide addition the reaction mass was stirred slowly overnight. Filtration of the reaction mass was rapid (580 ml in <15 min) yielding a nearly water white solution of 2-ethylhexyllithium. The filtration residues were washed once with 150 ml pentane which was combined with the main filtrate.

| Analyses: | |
|---|---|
| Total Base | = 0.94M (17.2 wt. %) |
| NMR | = 17.6 wt. % EHL |
| Density | = 0.657 g/cc |
| Li (ICP) | = 0.93M |
| Na (ICP) | = 8 ppm |
| Inorganic chloride | = 50 ppm |
| Organic chloride (GC) | = 1500 ppm EHC |
| Yield | = 94.8% (based on alkyl halide) |

The 2-ethylhexyllithium solution was concentrated from 17.2 wt % to 92.9 wt % by vacuum distillation. The concentrate was a slightly viscous, pourable liquid at ambient temperature (absolute viscosity=34.5 cp at 40° C. and 275 cp at 1.5° C.) and remained a mobile liquid when placed in a freezer overnight (−20° C.). It was observed during pyrophoricy testing that the 2-ethylhexyllithium concentrate just slightly charred the filter paper as compared to lower chain alkyllithiums, which cause filter paper to spontaneously inflame.

This Example was repeated employing different lithium/sodium mole ratios and various solvents and the results are reported in Tables I and IV. This Example was also repeated using different lithium/sodium mole ratios, various solvents and two different linear alkyl chlorides in place of 2-ethylhexylchloride and the results reported in Table V.

B. Synthesis of 2-Ethylhexyllithium (Exemplary Run 300-58)

Procedures

Lithium dispersion (2.16 moles) was washed in a glass filter funnel with two 100 ml aliquots of pentane and then transferred to the reaction vessel along with 500 ml pentane. The reaction was initiated with n-butyl chloride (1.5 g) as evidenced by a temperature rise of 5.3° C. The reaction mass was stirred for seven minutes and then 2-ethylhexyl chloride (2 g) was added. After noting no evidence of reaction (heat) after three minutes, 2-ethylhexyl chloride (1 g) was again added. Again, there was no evidence of reaction after an additional three minutes (Temp.=27° C.). The reaction mass was then brought to reflux (35.9° C.), and more 2-ethylhexyl chloride (2 g) was added. The reflux quickly subsided, and there was no evidence of reaction after stirring for an additional three hours. Attempts to initiate the reaction with 2-ethylhexyl chloride (3 g) failed during the next two hours. Next, sodium dispersion in oil (containing 0.97 mole Na) was transferred to the reaction vessel and stirred for 10 minutes. This time the addition of 2-ethylhexyl chloride (1 g) resulted in immediate reaction as evidenced by a rise in temperature of 4° C. The remaining 2-ethylhexyl chloride (114 g) was added over a period of 166 minutes while maintaining the reaction temperature at reflux. The reaction mass was stirred for an additional two hours and then filtered. Filtration was rapid yielding a yellow solution of 2-ethylhexyllithium in pentane.

| Analytical Results: | |
|---|---|
| Total Base | = 1.87M |
| W. E. Titration | = 1.86M |
| Li (ICP) | = 1.76M |
| Na (ICP) | = 1 ppm |
| Inorganic chloride | = 610 ppm |
| NMR | = 1.89M |
| Yield | = 88.4% recovered |

C. Preparation of 2-Methylbutyllithium

Example A, exemplary run 361-29, was repeated using 2-methylbutyl chloride in place of 2-ethylhexyl chloride which is reported in Table II, Experiment number 361-98; a comparative example using low levels of sodium was conducted and reported in Table II as Experiment 6811.

Exemplary Run 300-58 of the herein Examples shows that lithium containing alloying amounts of sodium (0.75% by weight) does not react with 2-ethylhexyl chloride. The beneficial effects on the reaction rate between lithium and alkyl chlorides due to 0.03 to 2 weight percent of sodium in the lithium does not occur with 2-alkyl substituted alkyl chlorides. Moreover, the comparison examples herein show that using lithium and sodium in equimolar and near equimolar amounts results in a reaction product mixture that is difficult to filter and contains unacceptably high levels of sodium. Thus, it is unexpected that using sodium in a molar range of 10 to 30% by weight based on lithium, and most beneficially 15 to 20%, would result in high yields in 2-alkyllithium production; the yields are higher than those achieved in producing 2-alkyl-substituted alkyllithiums by using 33 to 50% sodium in the Borkowski process.

COMPARISON EXAMPLES

The process of Example 1 of U.S. Pat. No. 3,293,313 was repeated several times using n-butyl chloride, reaction temperatures of 0° to 30° C. and various molar ratios of lithium and sodium metals. Details are reported in Table III with the yields being reported on the basis of the n-butyl chloride used unless stated otherwise.

Equimolar or near equimolar reactions produce very fine particle size by-product lithium chloride which is very difficult to filter and the solution products contain high levels of sodium.

TABLE I

Synthesis of 2-Ethylhexyllithium from the Halide and Li/Na Dispersion in Various Solvents

| Exp. No. | Li moles | Na moles | Li/Na mole Ratio | 2-Ethylhexyl Chloride moles | Solvent Type | ml | Total Base N. | Inorg. Cl Titration ppm | Na (ICP) ppm | Recovered yield % | 2-EHC (gc)[5] mole % |
|---|---|---|---|---|---|---|---|---|---|---|---|
| 300-58 | 2.16[1] | 0.97[1] | 69/31 | 0.83 | Pentane | 500 | 1.76 | 610 | 1 | 88.4 | N/A[6] |
| 300-62[4] | 1.78[1] | 0.90[1] | 66/34 | 1.22 | Cyclohexane | 608 | 1.28 | N/A | 2 | 68.2 | N/A |
| 361-14 | 2.30[2] | 0.98[2] | 70/30 | 1.2 | Pentane | 650 | 1.57 | 505 | 20 | 87.2 | 1.1 |
| 6687 | 1.96[2] | 0.84[2] | 70/30 | 0.90 | Cyclohexane | 540 | 1.31 | 1103 | 86 | 80.4 | 2.1 |
| 361-26 | 2.84[2] | 0.32[2] | 90/10 | 1.32 | Pentane | 500 | 1.54 | 900 | 25 | 77.0 | 8.5 |
| 6706 | 1.13[3] | 0.12[3] | 90/10 | 0.45 | Cyclohexane | 300 | 0.39 | 94 | 9 | 45.6 | 47.9 |
| 6708 | 1.13[3] | 0.24[3] | 83/17 | 0.50 | Cyclohexane | 300 | 0.94 | 5 | 14 | 89.9 | 1.4 |
| 361-29 | 1.167[3] | 0.239[3] | 83/17 | 0.50 | Pentane | 300 | 0.94 | 50 | 8 | 94.8 | 0.6 |

[1]Separately prepared lithium dispersion (0.75% Na) in mineral oil was mixed with sodium disperion in mineral oil.
[2]A lithium/sodium dispersion (70/30 mole %) was prepared employing mineral oil.
[3]The lithium and sodium dispersions were prepared and washed separately and mixed prior to reaction.
[4]Exp. No. 300-62 is a comparison example.
[5]The amount of unreacted 2-ethylhexyl chloride in the product solution based on the amount employed.
[6]N/A = not available.

TABLE II

SYNTHESIS OF 2-METHYLBUTYLLITHIUM FROM 2-METHYLBUTYLCHLORIDE AND LI/NA DISPERSIONS IN CYCLOHEXANE

| | Reagents | | | | | Results | | | |
|---|---|---|---|---|---|---|---|---|---|
| Exp. No. | Li[1] mole | Na moles | Li/Na mole ratio | 2-Methylbutyl Chloride moles | Cyclohexane mls | Total Base M | Active C—Li[3] M | Na[4] ppm | Yield[5] % |
| 6811 | 1.0 | 0 | 99.8/0.2 | 0.25 | 110 | 1.24 | 1.18 | — | 65.5 |
| 361-98 | 1.0 | 0.20[2] | 83/17 | 0.50 | 200 | 1.34 | 1.30 | 15 | 81.2 |

[1]The lithium dispersion contained 0.75% by-weight alloyed sodium.
[2]The sodium dispersion washed with cyclohexane and then mixed with the washed lithium dispersion.
[3]Active carbon-bound lithium; Watson, S. C. and Eastman, J. F., J. Organometallic Chem., 9, 165, (1967).
[4]Sodium determined by ICAP.
[5]Recovered yield based on the amount of 2-methylbutyl chloride used.

TABLE III n-BUTYLLITHIUM PREPARATIONS IN HYDROCARBON SOLVENT WITH LITHIUM-SODIUM MIXTURES

| Exp. No. | Li:Na, Mole Ratio | React. Temp. °C. | Rx. Mix. Settling Rate | Rx. Mix. Filtration Rate | NBL Yield % (on BuCl) | Product Molarity | Product Color | Sodium in Product Mole % | Li:Na Mole Ratio |
|---|---|---|---|---|---|---|---|---|---|
| A | 47:53[1] | 0 | Slow | V. Slow | 86[5] | 2.15 | [9] | 3.43 | 28:1 |
| B | 55:45[2],[3] | 30–35 | Slow | Slow[8] | 96[5] | 2.95 | [7] | 0.07 | 1420:1 |
| C | 50:50[2],[4] | 20–30 | Fair | Fair | 74[6] | 1.58 | [10] | 8.8 | 10.4:1 |
| D | 90:10 | 30–35 | Fast | Fast[11] | 92 | 2.88 | [7] | <0.01 | <10000:1 |

[1] Dispersion prepared from mixed metals.
[2] Dispersions prepared separately, then mixed.
[3] The lithium dispersion contained 0.37 wt. % Na.
[4] The lithium dispersion contained 2 wt. % sodium.
[5] Yield calculated on total volume of salts and solution.
[6] Yield calculated on recovered solution after filtration.
[7] Light yellow solution.
[8] Filtered 400 ml in 3.5 hrs.
[9] Deep orange.
[10] Dark orange-red solution.
[11] Filtered 580 ml in 6 minutes.

TABLE IV

SYNTHESIS OF 2-ALKYL-SUBSTITUTED ALKYLLITHIUMS EMPLOYING VARYING AMOUNTS OF LITHIUM AND SODIUM

| Alkyl Chloride | Li/Na mole ratio | Solvent Type | % Yield[1] (RLi) | Mass Balance Hydrolysate RH[4] | RCl[5] | R—R[6] | Na[2] ppm | Cl[3] ppm |
|---|---|---|---|---|---|---|---|---|
| 2-Ethylhexyl | 99.8/0.2 | Pentane | — | | no reaction | | — | — |
| 2-Ethylhexyl | 90/10 | Pentane | 77 | 86 | 9 | 5 | 25 | 900[8] |
| 2-Ethylhexyl | 90/10 | Cyclohexane | 46 | 51 | 48 | 1 | 9 | 94 |
| 2-Ethylhexyl | 83/17 | Pentane | 95 | 98 | 0.6 | 1.6 | 8 | 50 |
| 2-Ethylhexyl | 83/17 | Heptane | 86 | | N/A[7] | | N/A | |
| 2-Ethylhexyl | 83/17 | Cyclohexane | 90 | 97 | 1.4 | 1.5 | 14 | 5 |
| 2-Methylbutyl | 99.8/0.2 | Cyclohexane | 65 | | N/A | | N/A | |
| 2-Methylbutyl | 83/17 | Cyclohexane | 85 | | N/A | | 15 | N/A |

[1] Yield based on amount of halide employed.
[2] Sodium determined by ICAP.
[3] Soluble inorganic chloride determined by Mohr Titration.
[4] RH is hydrocarbon from hydrolysis of RLi.
[5] RCL is unreacted organic halide.
[6] R—R is Wurtz coupling product.
[7] N/A = Analysis is not available.
[8] Solution hazy due to incomplete filtration.

TABLE V

SYNTHESIS OF PRIMARY STRAIGHT CHAIN ALKYLLITHIUMS EMPLOYING VARYING AMOUNTS OF LITHIUM AND SODIUM

| Alkyl Chloride | Li/Na mole ratio | Solvent Type | % Yield[1] (RLi) | Mass Balance Hydrolysate RH[4] | RCl[5] | R—R[6] | Na[2] ppm | Cl[3] ppm |
|---|---|---|---|---|---|---|---|---|
| n-Octyl | 99.5/0.5 | Cyclohexane | 70 | 68 | 23 | 9 | 13 | 287 |
| n-Octyl | 90/10 | Cyclohexane | 58[8] | 70 | 0.4 | 11 | N/A | |
| n-Octyl | 80/20 | Toluene | 88 | 97 | 1 | 2 | 4 | 172 |
| n-Octyl | 80/20 | Pentane | 51[8] | 60 | 0.2 | 1.5 | N/A | |
| n-Butyl | 99.8/0.2 | Hexane | 91 | | N/A | | 21 | 395 |
| n-Butyl | 99.4/0.6 | Hexane | 92 | | N/A | | 14 | 232 |
| n-Butyl | 97/3 | Hexane | 90 | 98.6 | 0.02 | 1.3 | 9 | 32 |
| n-Butyl | 95/5 | Hexane | 91 | | N/A | | 3 | 87 |
| n-Butyl | 90/10 | Hexane | 92 | | N/A | | 7 | 42 |
| n-Butyl | 60/40 | Hexane | 82 | | N/A | | 118 | 11 |

[1] Yield based on amount of halide employed.
[2] Sodium determined by ICAP.
[3] Soluble inorganic chloride determined by Mohr Titration.
[4] RH is hydrocarbon from hydrolysis of RLi.
[5] RCL is unreacted organic halide.
[6] R—R is Wurtz coupling product.
[7] N/A = Analyis is not available.
[8] Sodium alkyl insoluble causing incomplete metal/metal exchange.

What is claimed is:

1. A process for the preparation of alkyllithium compounds by reacting in a liquid organic solvent, in an inert atmosphere a $C_2$ to $C_{18}$ saturated, acyclic, primary alkyl halide in which the improvement comprises reacting the primary halide with a dispersion of particulate lithium and sodium metals in which there is 5 to 30 mole percent sodium based on the lithium content at a temperature of 0° to a temperature up to but not exceeding the decomposition temperature of the product alkyllithium compound.

2. A process according to claim 1 wherein the reaction temperature is between 0° C. and 70° C.

3. A process according to claim 1 wherein the reaction temperature is between 30° C. and 40° C.

4. A process according to claim 1 wherein there is 10 mole percent to 30 mole percent sodium present based on the lithium content.

5. A process according to claim 1 wherein the $C_2$ to $C_{18}$ primary alkyl halide is $C_4$ to $C_{18}$ 2-alkyl-substituted alkyl halide.

6. The process according to claim 5 wherein the 2-alkyl-substituted alkyl halide is 2-ethylhexyl chloride.

7. A process according to claim 1 wherein the liquid organic solvent is selected from aliphatic hydrocarbons containing 5 to 10 carbon atoms, alicyclic hydrocarbons containing 5 to 10 carbon atoms, aromatic hydrocarbons containing 6 to 10 carbon atoms, mixed paraffinic hydrocarbons having boiling points below 130° C. and mixtures thereof.

8. A process according to claim 1 wherein there is 15 mole percent to 20 mole percent sodium present based on the lithium content.

* * * * *